United States Patent [19]

Zelle et al.

[11] Patent Number: 5,744,485
[45] Date of Patent: Apr. 28, 1998

[54] CARBAMATES AND UREAS AS MODIFIERS OF MULTI-DRUG RESISTANCE

[75] Inventors: Robert Edward Zelle, Stow; Matthew W. Harding, Acton, both of Mass.

[73] Assignee: Vertex Pharmaceuticals Incorporated, Cambridge, Mass.

[21] Appl. No.: 377,283

[22] Filed: Jan. 23, 1995

Related U.S. Application Data

[63] Continuation-in-part of Ser. No. 218,120, Mar. 25, 1994, abandoned.

[51] Int. Cl.$^6$ .................. C07D 211/32; A61K 31/445
[52] U.S. Cl. .................. 514/318; 514/237.2; 514/314; 514/315; 514/330; 546/153; 546/192; 546/193; 546/194; 546/245; 544/129
[58] Field of Search .................. 546/153, 192, 546/193, 194, 245; 544/129; 514/237.2, 314, 315, 318, 330

[56] References Cited

FOREIGN PATENT DOCUMENTS 019593  11/1992  WIPO .................. 546/153

OTHER PUBLICATIONS

Callens, Bull Soc. Chim Belg. vol. 91, No. 8, pp. 713–723, 1982.

Tozuka et al., J. of Antibiotics, vol. XXXVI, No. 12, pp. 1699–1708, 1983.

Chemical Abstracts, vol. 116, Abstract No. 256054p, Jun. 22, 1992.

*Primary Examiner*—Zinna Northington Davis
*Attorney, Agent, or Firm*—Fish & Neave; James F. Haley, Jr.

[57] ABSTRACT

The present invention relates to compounds that can maintain, increase, or restore sensitivity of cells to therapeutic or prophylactic agents. This invention also relates to pharmaceutical compositions comprising these compounds. The compounds and pharmaceutical compositions of this invention are particularly well-suited for treatment of multi-drug resistant cells, for prevention of the development of multi-drug resistance, and for use in multi-drug resistant cancer therapy.

19 Claims, No Drawings

CARBAMATES AND UREAS AS MODIFIERS OF MULTI-DRUG RESISTANCE

CROSS-REFERENCE TO PRIOR APPLICATION

This application is a continuation-in-part of application Ser. No. 218,120, filed Mar. 25, 1994 now abandoned.

TECHNICAL FIELD OF THE INVENTION

The present invention relates to novel compounds which can maintain, increase, or restore sensitivity of cells to therapeutic or prophylactic agents. This invention also relates to pharmaceutical compositions comprising these compounds. The compounds and pharmaceutical compositions of this invention are particularly well-suited for treatment of multi-drug resistant cells, for prevention of the development of multi-drug resistance and for use in multi-drug resistant cancer therapy.

BACKGROUND OF THE INVENTION

A major problem affecting the efficacy of chemotherapy regimens is the evolution of cells which, upon exposure to a chemotherapeutic drug, become resistant to a multitude of structurally unrelated drugs and therapeutic agents. The appearance of such multi-drug resistance often occurs in the presence of overexpression of the 170-kDA membrane P-glycoprotein (gp-170). The gp-170 protein is present in the plasma membranes of some healthy tissues, in addition to cancer cell lines, and is homologous to bacterial transport proteins (Hait et al., Cancer Communications, Vol. 1(1), 35 (1989); West, TIBS, Vol. 15, 42 (1990)). The protein acts as an export pump, conferring drug resistance through active extrusion of toxic chemicals. Although the mechanism for the pump is unknown, it is speculated that the gp-170 protein functions by expelling substances that share certain chemical or physical characteristics, such as hydrophobicity, the presence of carbonyl groups, or the existence of a glutathione conjugate (see West).

Recently, another protein responsible for multidrug resistance, MRP (multidrug resistance associated protein), was identified in H69AR cells, an MDR cell line that lacks detectable P-glycoprotein [S. P. C. Cole et al., Science, 258, pp. 1650–54 (1992)]. MRP has also been detected in other non-P-glycoprotein MDR cell lines, such as HL60/ADR and MCF-7 brast carcinoma cells [(E. Schneider et al., Cancer Res., 54, pp. 152–58 (1994); and N. Krishnamachary et al., Cancer Res., 53, pp. 3658–61 (1993)].

The MRP gene encodes a 190 kD membrane-associated protein that is another member of the ATP binding cassette superfamily. MRP appears to function in the same manner as P-glycoprotein, acting as a pump for removing natural product drugs from the cell. A possible physiological function for MRP maybe ATP-dependent transport of glutathione S-conjugates [G. Jedlitschky et al., Cancer Res., 54, pp. 4833–36 (1994); I. Leier et al., J. Biol. Chem., 269, pp. 27807–10 (1994); and Muller et al., Proc. Natl. Acad. Sci. USA, 91, pp. 13033–37 (1994)].

The role of MRP in clinical drug resistance remains to be clearly defined, but it appears likely that MRP may be another protein responsible for a broad resistance to anti-cancer drugs.

Various chemical agents have been administered to repress multi-drug resistance and restore drug sensitivity. While some drugs have improved the responsiveness of multi-drug resistant ("MDR") cells to chemotherapeutic agents, they have often been accompanied by undesirable clinical side effects (see Hait et al.). For example, although cyclosporin A ("CsA"), a widely accepted immunosuppressant, can sensitize certain carcinoma cells to chemotherapeutic agents (Slater et al., Br. J. Cancer, Vol. 54, 235 (1986)), the concentrations needed to achieve that effect produce significant immunosuppression in patients whose immune systems are already compromised by chemotherapy (see Hait et al.). In addition, CsA usage is often accompanied by adverse side effects including nephrotoxicity, hepatotoxicity and central nervous system disorders. Similarly, calcium transport blockers and calmodulin inhibitors both sensitize MDR cells, but each produces undesirable physiological effects (see Hait et al.; Twentyman et al., Br. J. Cancer, Vol. 56, 55 (1987)).

Recent developments have led to agents said to be of potentially greater clinical value in the sensitization of MDR cells. These agents include analogs of CsA which do not exert an immunosuppressive effect, such as 11-methyl-leucine cyclosporin (11-met-leu CsA) (see Hait et al.; Twentyman et al.), or agents that may be effective at low doses, such as the immunosuppressant FK-506 (Epand and Epand, Anti-Cancer Drug Design 6, 189 (1991)). Despite these developments, the need remains for effective agents which may be used to resensitize MDR cells to therapeutic or prophylactic agents or to prevent the development of multi-drug resistance.

SUMMARY OF THE INVENTION

The present invention provides novel compounds that are useful to maintain, increase or restore drug sensitivity in multi-drug resistant ("MDR") cells, compositions containing those compounds and methods for using them. The compounds of this invention may be used alone or in combination with other therapeutic or prophylactic agents to maintain, increase or restore the therapeutic or prophylactic effects of drugs in cells, especially MDR cells, or to prevent the development of MDR cells. According to one embodiment of this invention, these novel compounds, compositions and methods are advantageously used to aid or enhance chemotherapy regimens for the treatment or prophylaxis of cancer and other diseases.

The present invention also provides methods for preparing the compounds of this invention and intermediates useful in those methods.

DETAILED DESCRIPTION OF THE INVENTION

This invention relates to a novel class of compounds represented by formula (I):

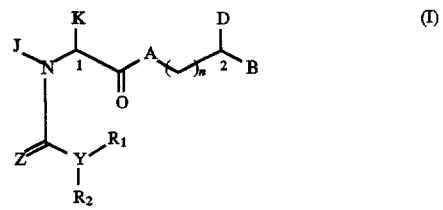

wherein A is $CH_2$, oxygen, NH or N—(C1–C4 alkyl);
wherein B and D are independently:
  Ar, (C1–C6)-straight or branched alkyl, (C2–C6)-straight or branched alkenyl or alkynyl, (C5–C7)-cycloalkyl substituted (C1–C6)-straight or branched alkyl, (C3–C6)-straight or branched alkenyl or alkynyl, (C5–C7)-cycloalkenyl substituted (C1–C6)-straight or branched alkyl, (C3–C6)-straight or branched alkenyl or alkynyl, Ar-substituted (C1–C6)-straight or branched alkyl, Ar-substituted (C3–C6)-straight or branched alkenyl or alkynyl, wherein any one of the $CH_2$ groups of said alkyl chains may be optionally replaced by a heteroatom selected from the group consisting of O, S, SO, $S_2$, and NR, wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group;

J is selected from the group consisting of hydrogen, (C1–C6)-straight or branched alkyl, (C3–C6)-straight or branched alkenyl and —$CH_2$Ar;

K is selected from the group consisting of (C1–C4)-straight or branched alkyl, —$CH_2$Ar and cyclohexylmethyl;

or J and K may be taken together to form a 5–7 membered heterocyclic ring which may contain a heteroatom selected from the group consisting of O, S, SO and $SO_2$;

Z is O or S;

Y is O or N, wherein when Y is O then $R_1$ is a lone pair (as used herein, the term "lone pair" refers to a lone pair of electrons, such as the lone pair of electrons present on divalent oxygen) and $R_2$ is selected from the group consisting of Ar, (C1–C6)-straight or branched alkyl, and (C3–C6)-straight or branched alkenyl or alkynyl; and when Y is N, then $R_1$ and $R_2$ are independently selected from the group consisting of Ar, (C1–C6)-straight or branched alkyl, and (C3–C6)-straight or branched alkenyl or alkynyl; or $R_1$ and $R_2$ are taken together to form a heterocyclic 5–6 membered ring selected from the group consisting of pyrrolidine, imidazolidine, pyrazolidine, piperidine, and piperazine;

wherein Ar is a carbocyclic aromatic group selected from the group consisting of phenyl, 1-naphthyl, 2-naphthyl, indenyl, azulenyl, fluorenyl, and anthracenyl;

or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydro-quinolinyl, isoquinolinyl, 1,2,3,4-tetrahydro-isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar may contain one or more substituents which are independently selected from the group consisting of hydrogen, halogen, hydroxyl, nitro, —$SO_3H$, trifluoromethyl, trifluoromethoxy, (C1–C6)-straight or branched alkyl, (C2–C6)-straight or branched alkenyl, O—[(C1–C6)-straight or branched alkyl], O—[(C3–C4)-straight or branched alkenyl], O-benzyl, O—phenyl, 1,2-methylenedioxy, —$NR_3R_4$, carboxyl, N-(C1–C5-straight or branched alkyl or C3–C5-straight or branched alkenyl) carboxamides, N,N-di-(C1–C5-straight or branched alkyl or C3–C5-straight or branched alkenyl) carboxamides, morpholinyl, piperidinyl, O—X, $CH_2$—$(CH_2)_q$—X, O—$(CH_2)_q$—X, $(CH_2)_q$—O—X, and CH=CH—X;

wherein $R_3$ and $R_4$ are independently selected from the group consisting of (C1–C6)-straight or branched alkyl, (C3–C6)-straight or branched alkenyl, hydrogen and benzyl; or wherein $R_3$ and $R_4$ can be taken together to form a 5–6 membered heterocyclic ring such as, for example, piperidinyl, morpholinyl or pyrrolidinyl, X is selected from the group consisting of 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, and pyrimidyl; q is 0–2; and n is 0 or 1.

As used herein for $R_3$ and $R_4$, the term "heterocyclic" refers to a stable 5–6 membered monocycle or 8–11 membered bicyclic heterocycle which is either saturated or unsaturated, and which may be optionally benzofused if monocyclic. Each heterocycle consists of carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. The heterocyclic ring may be attached by any heteroatom of the cycle which results in the creation of a stable structure. Typical examples of such heterocycles include piperdinyl, morpholinyl or pyrrolidinyl.

Preferably, at least one of B or D is independently a straight chain terminated by an aryl group, i.e., a group represented by the formula—$(CH_2)_r$—(X)—$(CH_2)_s$—Ar, wherein r is 1–4;

s is 0–1;

Ar is as defined above; and each X is independently selected from the group consisting of $CH_2$, O, S, SO, $SO_2$, and NR, wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen atom and the Ar group.

The preferred Ar groups of this invention include phenyl, 2-pyridyl, 3-pyridyl, 4-pyridyl, indolyl, isoindolyl, quinolinyl, isoquinolinyl, 1,2,3,4-tetrahydroisoquinolinyl, and 1,2,3,4-tetrahydroquinolinyl, wherein the Ar groups may contain one or more substituents which are independently selected from the group consisting of hydrogen, hydroxyl, nitro, trifluoromethyl, (C1–C6)-straight or branched alkyl, O—[(C1–C6)-straight or branched alkyl], halogen, $SO_3H$, and $NR_3R_4$, wherein $R_3$ and $R_4$ are independently selected from the group consisting of (C1–C6)-straight or branched alkyl, (C3–C6)-straight or branched alkenyl, hydrogen and benzyl; or wherein $R_3$ and $R_4$ can be taken together to form a 5–6 membered heterocyclic ring such as, for example, piperidinyl, morpholinyl or pyrrolidinyl.

Examples of some preferred compounds of formula (I), wherein J and K are taken together to form a 5–7 membered heterocyclic ring, have the formula (II) or (III), wherein Y, $R_1$ and $R_2$ are as defined above for formula (I), Ar is defined as above for preferred Ar groups and w is 1 or 2.

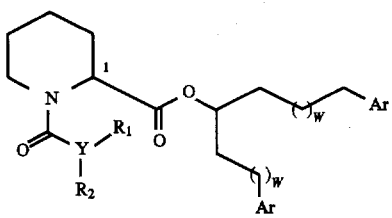
(II)

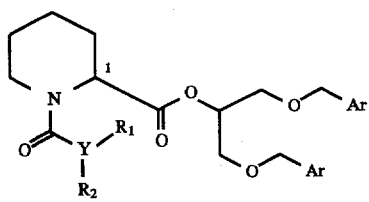
(III)

Examples of some preferred compounds of formula (I), wherein J is independently hydrogen, (C1–C6) straight or branched alkyl or (C3–C6) straight or branched alkenyl, have the formula (II') or (III'), wherein Y, $R_1$ and $R_2$ are as defined above for formula (I) and Ar is as defined above for preferred Ar groups and w is 1 or 2.

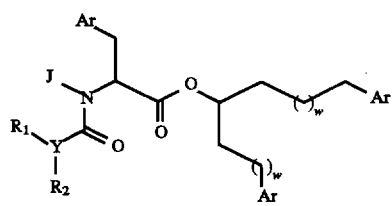
(II')

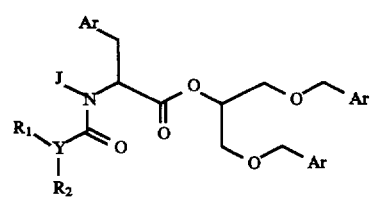
(III')

As used herein, the compounds of this invention, including the compounds of formula (I), are defined to include pharmaceutically acceptable derivatives thereof. A "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to maintain, increase or restore sensitivity of MDR cells to therapeutic or prophylactic agents or to prevent development of multi-drug resistance.

Compounds of this invention, including those represented by formula (I), may be obtained using any conventional technique. Preferably, these compounds are chemically synthesized from readily available starting materials, such as alpha-amino acids. Modular and convergent methods for the synthesis of these compounds are also preferred. In a convergent approach, for example, large sections of the final product are brought together in the last stages of the synthesis, rather than by incremental addition of small pieces to a growing molecular chain.

Scheme 1 illustrates a representative example of a convergent process for the synthesis of compounds of formula (I'), a preferred subset of compounds of formula (I), wherein A and Z are oxygens. The process comprises esterification of a protected alpha-amino acid of formula (X), wherein P is a protecting group, with an alcohol of formula (XI). Protected alpha-amino acids are well known in the art and many are commercially available. For example, common protecting groups and convenient methods for the protection of amino acids are described in T. W. Greene, P. G. M. Wuts, Protective Groups in Organic Chemistry, 2nd Ed., John Wiley and Sons, New York (1991). Alkoxycarbonyl groups are preferred for protection of the nitrogen atom in compounds of formula (X), with t-butoxycarbonyl (Boc), benzyloxycarbonyl (Cbz), allyloxycarbonyl (Alloc), and trimethylsilylethoxycarbonyl (Teoc) being more preferred.

After esterification, compounds of formula (XII) are deprotected under suitable deprotection conditions (see Greene, supra), and the free amino group of (XIII) is then acylated using a preformed acyl chloride of formula (XIV) to give a compound of formula (I'). The halogen chloro group in (XIV) may be replaced with other leaving groups or activating groups known in the art such as other halogens, imidazolyl or pentafluorophenoxy groups.

Alcohols of formula (XI) wherein m is 0 (XI') can also be conveniently prepared, for example, as illustrated in Schemes 2 and 3. Reaction of an organometallic reagent of formula (XV) and an aldehyde of formula (XVI) provides alcohols of formula (XI') (Scheme 2).

Alternatively (Scheme 3), 1,6-heptadiyn-4-ol can be coupled via a metal-catalyzed reaction to aromatic halides of formula (XVII) to give an alcohol of formula (XVIII). Subsequent hydrogenation provides an alcohol of formula (XI"), a preferred subset of alcohols of formula (XI).

Scheme 1

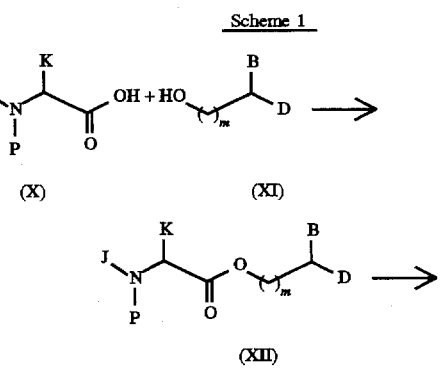

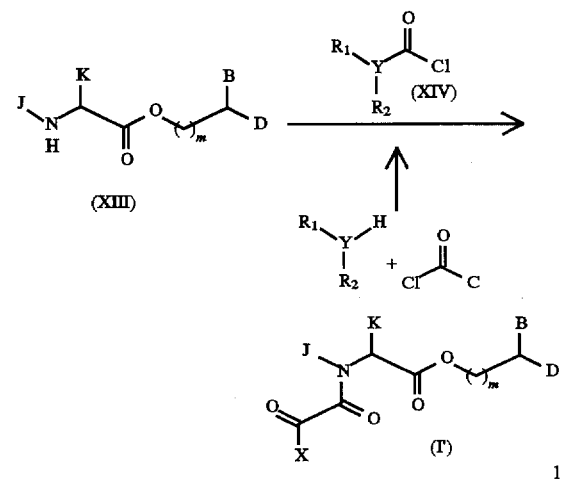

Scheme 2

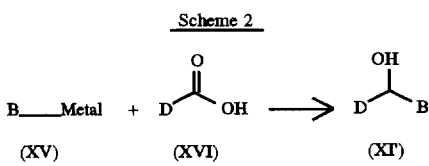

Scheme 3

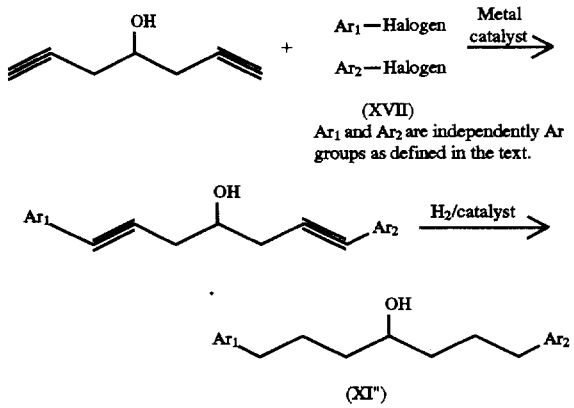

Ar₁ and Ar₂ are independently Ar groups as defined in the text.

Thus, this invention also provides a method for preparing compounds of formula (I') comprising the steps of:

(a) esterifying a protected amino acid of formula (X) with an alcohol of formula (XI) to give an intermediate of formula (XII);

(b) deprotecting the amino protecting group in the intermediate of formula (XII) to give an amino ester of formula (XIII); and (c) acylating the free amino group in the compound of formula (XIII) with an acyl halide of formula (XIV) or other activated derivatives thereof.

It should be appreciated by those of ordinary skill in the art that a large variety of compounds of formula (I) may be readily prepared, according to the processes illustrated in synthetic Schemes 1 and 2. The same processes may be used for the synthesis of many different end-products, by altering the variables in the starting materials.

Optically active compounds of formula (I) may also be prepared using optically active starting materials, thus obviating the need for resolution of enantiomers or separation of diastereomers at a late stage in the synthesis.

It will also be appreciated by those of ordinary skill in the art that the above synthetic schemes are not intended to comprise a comprehensive list of all means by which the compounds or the intermediates of this invention may be synthesized. Further methods or modifications of the above general schemes will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of this invention are characterized by the ability to increase, restore or maintain the sensitivity of MDR cells to cytotoxic compounds, such as, for example, those typically used in chemotherapy. Based on that ability, the compounds of this invention are advantageously used as chemosensitizing agents, to increase the effectiveness of chemotherapy in individuals who are afflicted with drug-resistant cancers, tumors, metastases or disease. In addition, the compounds of this invention are capable of maintaining sensitivity to therapeutic or prophylactic agents in non-resistant cells. Therefore, the compounds of this invention are useful in treating or preventing multi-drug resistance in a patient. More specifically, these compounds are useful intreating of preventing P-glycoprotein-mediated MDR and MRP-mediated MDR.

As used throughout this application, the term "patient" refers to mammals, including humans. And the term "cell" refers to mammalian cells, including human cells.

As used herein, the terms "sensitizing agent", "sensitizer", "chemosensitizing agent", "chemosensitizer" and "MDR modifier" denote a compound having the ability to increase or restore the sensitivity of an MDR cell, or to maintain the sensitivity of a non-resistant cell, to one or more therapeutic or prophylactic agents. The term "MDR sensitization" and "sensitization" and "resensitization" refer to the action of such a compound in maintaining, increasing, or restoring drug sensitivity.

According to one embodiment of this invention, compounds that are useful in increasing, restoring or maintaining drug sensitivity are also capable of binding to the protein FKBP-12 or other related FK-506 binding proteins such as FKBP-13, FKBP-26 and FKBP-52. In vitro tests (data not shown) of these compounds demonstrate that the agents bind to FKBP-12. Thus, this invention also comprises a class of chemosensitizing agents other than FK-506, characterized by the ability to bind to the FK binding protein-12 or related FK binding proteins, pharmaceutical compositions including such agents and a physiologically acceptable adjuvant, carrier or vehicle, and methods of using those compositions for treating or preventing multi-drug resistance in a patient.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intrasynovial, intrasternal, intrathecal, intrahepatic, intralesional and intracranial injection or infusion techniques.

The pharmaceutical compositions of this invention comprise any of the compounds of the present invention, or pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered. The term "pharmaceutically effective amount" refers to an amount effective to prevent multi-drug resistance or maintain, increase or restore drug sensitivity in MDR cells. Dosage levels of between about 0.01 and about 100 mg/kg body weight per day, preferably between about 0.5 and about 50 mg/kg body weight per day of the active ingredient compound are useful. A typical preparation will contain between about 5% and about 95% active compound (w/w). Preferably, such preparations contain between about 20% and about 80% active compound.

When the compounds of this invention are administered in combination therapies with other agents, they may be administered sequentially or concurrently to the patient.

Alternatively, pharmaceutical or prophylactic compositions according to this invention may comprise a combination of a compound of this invention and another therapeutic or prophylactic agent.

For example, the compounds may be administered either alone or in combination with one or more therapeutic agents, such as chemotherapeutic agents, (e.g., actinomycin D, doxorubicin, vincristine, vinblastine, etoposide, amsacrine, mitoxantrone, tenipaside, taxol and colchicine) and/or a chemosensitizing agent (e.g., cyclosporin A and analogs, phenothiazines and thioxantheres), in order to increase the susceptibility of the MDR cells within the patient to the agent or agents.

In order that this invention may be more fully understood, the following examples are set forth. These examples are for the purpose of illustration only and are not to be construed as limiting the scope of the invention in any way.

EXAMPLES

General Methods

Proton nuclear magnetic resonance ($^1$H NMR) spectra were recorded at 500 MHz on a Bruker AMX 500. Chemical shifts are reported in parts per million ($\delta$) relative to Me$_4$Si ($\delta$0.0). Analytical high performance liquid chromatography was performed on either a Waters 600E or a Hewlett Packard 1050 liquid chromatograph.

Example 1

1,7-Dipyridin-3-yl-hept-1,6-diyne-4-ol (1)

A mixture of 1,6-heptadiyn-4-ol (25 g, 0.231 mol), palladium(II) acetate (2.6 g, 11.0 mmol), copper(I)iodide (3.3 g, 11.0 mmol) and triphenylphosphine (9.1 g, 35.0 mmol) in degassed triethylamine (300 mL) was treated with 3-bromopyridine (77 g, 0.49 mol). After stirring for 24 h at room temperature, the reaction was filtered through a plug of Celite and the Celite washed with ethyl acetate (EtOAc). The filtrate was concentrated to afford a dark brown oil. This material was dissolved in 2N hydrochloric acid (HCl) and washed with EtOAc (2x). The pH of the aqueous layer was adjusted to pH>8 by addition of 3N sodium hydroxide (NaOH) and then extracted with EtOAc (2x). The extracts were combined, washed with half-saturated aqueous sodium chloride, brine, dried over magnesium sulfate (MgSO$_4$), filtered and concentrated. The residue was passed through a plug of silica gel (SiO$_2$, elution with EtOAc) to provide 33.1 g of compound 1 as a solid upon drying.

Example 2

1,7-Dipyridin-3-yl-heptan-4-ol (2)

A suspension of platinum oxide (280 mg) in absolute ethanol (1 mL) was diluted with absolute methanol (10 mL) followed by the addition of compound 1 (2.81 g, 10.73 mmol). The suspension was placed under 40 psi of hydrogen gas. After hydrogen consumption ceased, the hydrogen was replaced with nitrogen and the reaction was filtered and concentrated to provide 2.87 g of compound 2 as a viscous oil.

Example 3

(S)-Piperidine-1,2-dicarboxylic acid 1-tert-butyl ester 2-(1-(3-pyridin-3-yl-propyl)-4-pyridin-3-yl)-butyl ester (3)

To a solution of compound 2 (9.5 g, 35.18 mmol) and (S)-piperidine-1,2 dicarboxylic acid 1-tert-butyl ester (12.1 g, 52.78 mmol), and N,N-dimethyl-4-aminopyridine (427 mg, 3.5 mmol) in methylene chloride (CH$_2$Cl$_2$, 50 mL) at 0° C. was added 1-(3-dimethylaminopropyl)-3-ethylcarbodiimide hydrochloride (10.1 g, 52.78 mmol). The reaction was warmed to room temperature and allowed to stir for 16 h. The reaction was diluted with EtOAc, washed with water, 5% aqueous sodium bicarbonate (NaHCO$_3$), brine, dried over anhydrous magnesium sulfate (MgSO$_4$) and concentrated to provide 16.67 g of compound 3 as a viscous oil.

Example 4

(S)-Piperidine-2-carboxylic acid 2-(1-(3-pyridin-3-yl-propyl)-4-pyridin-3-yl)-butyl ester (4)

To a solution of compound 3 (16.67 g, 34.66 mmol) in CH$_2$Cl$_2$ (40 mL) at 0° C. was added trifluoroacetic acid (40 mL). After the addition was complete, the reaction was warmed to room temperature and stirred for 4 h. The reaction was concentrated and the residue taken up into water and made basic with solid K$_2$CO$_3$. The product was extracted with CH$_2$Cl$_2$ (2x). The extracts were combined dried over MgSO$_4$, filtered and concentrated to provide 13.20 g of compound 4 as a viscous oil.

Example 5

(S)-1-((3,4,5-Trimethoxyphenyl)-methyl-carbamoyl)-piperidine-2-carboxylic acid 4-pyridin-3-yl-1-(3-pyridin-3-yl-propyl)-butyl ester (5)

To a mixture of N-methyl-3,4,5-trimethoxyaniline (130 mg, 0.66 mmol) and diisoproylethylamine (i-Pr$_2$NEt, 215 μL, 1.2 mmol) in methylene chloride (CH$_2$Cl$_2$, 1 mL) was added 1.2M phosgene in toluene (1.65 mL). After stirring for 2 h, the reaction was concentrated and placed under vacuum to remove residual phosgene. To a solution of compound 4 (225 mg, 0.59 mmol) in CH$_2$Cl$_2$ (1.5 mL) containing i-Pr$_2$EtN (215 μL, 1.2 mmol) was added the above preformed acyl chloride in CH$_2$Cl$_2$ (1.5 mL). After stirring for 1 h, the reaction was diluted with ethyl acetate (EtOAc), washed with 5% aq. NaHCO$_3$, brine, dried over MgSO$_4$, filtered and concentrated in vacuo to provide a viscous oil. Chromatography of the residue on SiO$_2$ (elution with 30 to 60% acetone:hexanes) provided 238 mg (67%) of compound 5 as a viscous oil. $^1$H NMR (500 MHz, CDCl$_3$) $\delta$8.44–8.40 (m, 4H), 7.35 (m, 2H), 7.22–7.18 (m, 2H), 6.43 (br s, 2H), 4.98 (m, 1H), 4.74 (m, 1H), 3.84 (s, 9H), 3.42 (br s, 1H), 3.18 (s, 3H), 2.92 (m, 1H), 2.65–2.56 (m, 5H), 2.06–1.98 (m, 1H), 1.70–153 (m, 15H).

Example 6

(S)-1-((3-Trifluoromethylphenyl)-methyl-carbamoyl)-piperidine-2-carboxylic acid 4-pyridin-3-yl-1-(3-pyridin-3-yl-propyl)-butyl ester (6)

Compound 6 was prepared according to the protocol of Example 5, except that N-methyl-3,4,5-trimethoxyaniline was replaced with N-methyl-3-trifluoromethylaniline. $^1$H NMR (500 MHz, CDCl$_3$) $\delta$8.42–8.39 (m, 4H), 7.50–6.16 (m, 10H), 4.99 (m, 1H), 4.64 (m, 1H), 3.29 (m, 1H), 3.20 (s, 3H), 2.93 (m, 1H), 2.67–2.53 (m, 4H), 2.03–1.99 (m, 1H), 1.69–1.53 (m, 13H).

Example 7

(S)-1-((4-Tert-butylphenyl)-methyl-carbamoyl)-piperidine-2-carboxylic acid 4-pyridin-3-yl-1-(3-pyridin-3-yl-propyl)-butyl ester (7)

Compound 7 was prepared according to the protocol of Example 5, except that N-methyl-3,4,5-trimethoxyaniline was replaced with N-methyl-4-tert-butylaniline. $^1$H NMR (500 MHz, CDCl$_3$) δ8.40 (m, 4H), 7.49–7.42 (m, 2H), 7.30 (d, 2H), 7.17 (m, 2H), 7.05 (d, 2H), 4.99 (m, 1H), 4.64 (m, 1H), 3.35 (m, 1H), 3.14 (s, 3H), 2.84 (dt, 1H), 2.64–2.52 m, 4H), 2.00–1.95 (m, 1H), 1.70–1.48 (m, 11H), 1.27 (s, 9H), 1.20–1.02 (m, 2H).

Example 8

(S)-1-((4-Isopropylphenyl)-methyl-carbamoyl)-piperidine-2-carboxylic acid 4-pyridin-3-yl-1-(3-pyridin-3-yl-propyl)-butyl ester (8)

Compound 8 was prepared according to the protocol of Example 5, except that N-methyl-3,4,5-trimethoxyaniline was replaced with N-methyl-4-iso-propylaniline. $^1$H NMR (500 MHz, CDCl$_3$) δ8.42–8.39 (m, 4H), 7.49–7.43 (m, 2H), 7.18 (m, 2H), 7.14 (d, 2H), 7.06 (d, 2H), 4.99 (m, 1H), 4.64 (m, 1H), 3.35 (br d, 1H), 3.15 (s, 3H), 2.85 (m, 2H), 2.59 (m, 4H), 1.97 (m, 1H), 1.70–1.49 (m, 11H), 1.21 (d, 6H), 1.20–1.02 (m, 2H).

Example 9

(S)-1-(Piperidine-1-carbonyl)-piperidine-2-carboxylic acid 4-pyridin-3-yl-1-(3-pyridin-3-yl-propyl)-butyl ester (9)

Compound 9 was prepared according to the protocol of Example 5, except that N-methyl-3,4,5-trimethoxyaniline was replaced with N-piperidine. $^1$H NMR (500 MHz, CDCl$_3$) δ8.42–8.39 (m, 4H), 7.50–7.43 (m, 2H), 7.24–7.16 (m, 2H), 4.98 (m, 1H), 4.67 (t, 1H), 3.32–3.09 (m, 8H), 2.64–2.52 (m, 6H), 2.01–1.96 (m, 1H), 1.80–1.30 (m, 15H).

Example 10

(S)-1-((3,4,5-Trimethoxyphenyl)-methyl-carbamoyl)-piperidine-2-carboxylic acid 4-pyridin-1-yl-1-(3-pyridin-1-yl-propyl)-butyl ester (10)

Compound 10 was prepared according to the protocols of Examples 1–5, except that 3-bromopyridine was replaced with 1-bromopyridine. $^1$H NMR (500 MHz, CDCl$_3$) δ8.50 (t, 2H), 7.56 (dq, 2H), 7.18–7.08 (m, 4H), 6.43 (s, 2H), 4.97 (q, 1H), 4.78 (m, 1H), 3.83 (s, 9H), 3.44 (br d, 1H), 3.19 (s, 3H), 2.89 (dt, 1H), 2.82–2.73 (m, 4H), 2.07 (br d, 1H), 1.81–1.52 (m, 12H).

Example 11

(S)-Piperidine-1,2-dicarboxylic acid 1-(3,4,5-trimethoxyphenyl) ester 2-(4-pyridin-3-yl-1-(3-pyridin-3-yl-propyl)-butyl) ester (11)

Compound 11 was prepared according to the protocol of Example 5, except that N-methyl-3,4,5-trimethoxyaniline was replaced with 3,4,5-trimethoxyphenol. Compound as a mixture of rotomers: $^1$H NMR (500 MHz, CDCl$_3$) δ8.42–8.35 (m), 7.50–7.32 (m), 7.28–7.18 (m), 6.34 (s), 6.27 (s), 5.34–4.90 (m), 4.19–4.01(m), 3.78 (s), 3.75 (s), 3.22 (br dt), 3.14 (quintet), 3.05–2.90 (m), 2.65–2.53 (m), 2.27–2.21 (m), 2.02 (s), 1.80–1.45 (m).

Example 12

(S)-Piperidine-2-carboxylic acid 2-(1-(2-phenyl-ethyl)-3-phenyl-propyl ester (12)

Compound 12 was prepared according to the protocols of Examples 3–4, except that compound 2 in Example 3 was replaced with 1,5-diphenylpentan-3-ol.

Example 13

(S)-1-((3,4,5-Trimethoxyphenyl)-methyl-carbamoyl)-piperidine-2-carboxylic acid 1-(2-phenyl-ethyl)-3-phenyl-propyl ester (13)

Compound 13 was prepared according to the protocol of Example 5, except that compound 4 was replaced with compound 12. $^1$H NMR (500 MHz, CDCl$_3$) δ7.27 (m, 4H), 7.20–7.14 (m, 6H), 6.47 (s, 2H), 5.01 (m, 1H), 4.87 (m, 1H), 3.84 (s, 6H), 3.83 (s, 3H), 3.48 (br d, 1H), 3.23 (s, 3H), 2.94 (dt, 1H), 2.72–2.44 (m, 4H), 2.17–2.10 (m, 1H), 2.00–1.85 (m, 4H), 1.67–1.60 (m, 2H), 1.45–1.40 (m, 1H), 1.30–1.18 (m, 2H).

Example 14

4-(Methyl-(2-(1-phenethyl-3-phenyl-propoxycarbonyl)-piperidine-1-carbonyl)-amino)-benzenesulfonic acid (14)

Compound 14 was prepared according to the protocol of Example 13, except that N-methyl-3,4,5-trimethoxyaniline was replaced with N-methyl-4-aminophenyl sulfonic acid.

Example 15

(S)-Piperidine-2-carboxylic acid 1-benzyloxymethyl-2-benzyloxyethyl ester (15)

Compound 15 was prepared according to the protocols of Examples 3–4, except that compound 2 in Example 3 was replaced with 1,3-dibenzyloxypropan-2-ol.

Example 16

(S)-1-(Methyl-(4-morpholin-1-yl-phenyl)-carbamoyl)-piperidine-2-carboxylic acid 2-benzyloxy-1-(benzyloxy-methyl)-ethyl ester (16)

Compound 16 was prepared according to the protocol of Example 5, except that compound 4 was replaced with compound 15 and N-methyl-3,4,5-trimethoxyaniline with N-methyl-4-morpholinoaniline. $^1$H NMR (500 MHz, CDCl$_3$) δ7.34–7.11 (m, 10H), 7.09 (d, 2H), 6.84 (d, 2H), 5.29 (quintet, 1H), 4.81 (br t, 1H), 4.54 (d, 2H), 4.49 (dd, 2H), 3.84 (t, 2H), 3.67 (t, 2H), 3.40 (br d, 1H), 3.15 (s, 3H), 3.09 (t, 4H), 2.86 (dt, 1H), 2.08–2.05 (m, 1H), 1.60–1.44 (m, 2H), 1.27–1.08 (m, 3H).

Example 17

(S)-1-(Methyl-(4-piperidin-1-yl-phenyl)-carbamoyl)-piperidine-2-carboxylic acid 2-benzyloxy-1-(benzyloxy-methyl)-ethyl ester (17)

Compound 17 was prepared according to the protocol of Example 16, except that N-methyl-3,4,5-trimethoxyaniline was replaced with N-methyl-4-piperdinoaniline. $^1$H NMR (500 MHz, CDCl$_3$) δ7.36–7.25 (m, 10H), 7.06 (d, 2H), 6.86 (d, 2H), 5.29 (quintet, 1H), 4.79 (m, 1H), 4.55–4.48 (m, 4H), 3.66 (m, 4H), 3.41 (br d, 1H), 3.14 (s, 3H), 3.10 (m, 4H), 2.87 (dt, 1H), 2.05 (br d, 1H), 1.73–1.67 (m, 4H), 1.61–1.45 (m, 4H), 1.25–1.08 (m, 3H).

Example 18

(S)-Piperidine-1,2-dicarboxylic acid 2-(2-benzyloxy-1-(benzyloxymethyl)-ethyl)ester 1-quinolin-5-yl ester (18)

Compound 18 was prepared according to the protocol of Example 16, except that N-methyl-3,4,5-trimethoxyaniline was replaced with 5-hydroxyquinoline. Compound 18 was a mixture of rotomers: $^1$H NMR (500 MHz, CDCl$_3$) δ8.89 (dd), 8.86 (dd), 8.90 (d), 8.24 (d), 7.89 (t), 7.67 (t), 7.63 (t), 7.36–7.18 (m), 5.44 (quintet), 5.36 (quintet), 5.20 (d), 5.02 (d), 4.56–4.44 (m), 4.34 (br d), 4.14 (br d), 3.72–3.56 (m), 3.39 (dt), 3.09 (dt), 2.38 (br t); 1.90–1.49 (m), 1.40–1.29 (m).

Example 19

(S)-Piperidine-1,2-dicarboxylic acid 2-(2-benzyloxy-1-(benzyloxymethyl)-ethyl)ester 1-pyridin-3-yl ester (19)

Compound 19 was prepared according to the protocol of Example 16, except that N-methyl-3,4,5-trimethoxyaniline was replaced with 3-hydroxypyridine. Compound 19 was a mixture of rotomers: $^1$H NMR (500 MHz, CDCl$_3$) δ8.46–8.41 (m), 7.48 (dt), 7.43 (dt), 7.34–7.24 (m), 7.18 (dd), 5.40–5.33 (m), 5.03 (dd), 4.57–4.47 (m), 4.17 (br d), 3.69–3.66 (m), 3.27 (dt), 3.05 (dt), 2.33 (br d), 1.81–1.71 (m), 1.69–1.64 (m), 1.56–1.43 (m), 1.35–1.27(m).

Example 20

2-(1,3-Dimethyl-3(3,4,5-trimethoxyphenyl)ureido)-3 phenyl-propanoic acid 4-pyridin-3-yl-1-(3-pyridin-3-yl-propyl)-butyl ester (20)

Compound 20 is prepared according to the protocols of Examples 3–5, by replacing (S)-piperidine-1,2-dicarboxylic acid 1-tert-butyl ester with N-(tert-butoxycarbonyl)-L-phenylalanine.

Example 21

2-(1,3-Dimethyl-3-(3,4,5-trimethoxyphenyl)ureido)-3-(phenyl)-propanoic acid 3-pyridin-3-yl-1-(2-pyridin-3-yl-ethyl)-propyl ester (21)

Compound 21 is prepared according to the protocols of Examples 3–5, by replacing (S)-piperidine-1,2-dicarboxylic acid 1-tert-butyl ester with N-(tert-butoxycarbonyl)-L-phenylalanine and 1,7-dipyridin-3-yl-heptan-4-ol with 1,5-dipyridin-3-yl-pentan-3-ol.

Example 22

N-Methyl-2-phenylethylamine-1,2-dicarboxylic acid 1-(3,4,5-trimethoxyphenyl) ester 2-(4-pyridin-3-yl-1-(3-pyridin-3-yl-propyl)butyl) ester (22)

Compound 22 is prepared according to the protocol of Example 20, by replacing N-methyl-3,4,5-trimethoxyaniline with 3,4,5-trimethoxyphenol.

Example 23

N-Methyl-2-phenylethylamine-1,2-dicarboxylic acid 1-(3,4,5-trimethoxyphenyl) ester 2-(3-pyridin-3-yl-1-(2-pyridin-3-yl-ethyl)propyl) ester (23)

Compound 23 is prepared according to the protocol of Example 21, by replacing N-methyl-3,4,5-trimethoxyaniline with 3,4,5-trimethoxyphenol.

Example 24

MDR SENSITIZATION ASSAYS

To assay the ability of the compounds according to this invention to increase the antiproliferative activity of a drug, cell lines which are known to be resistant to a particular drug may be used. These cell lines include, but are not limited to, the L1210, P388D, CHO and MCF7 cell lines. Alternatively, resistant cell lines may be developed. The cell line is exposed to the drug to which it is resistant, or to the test compound; cell viability is then measured and compared to the viability of cells which are exposed to the drug in the presence of the test compound.

We have carried out assays using L1210 mouse leukemia cells transformed with the pHaMDR1/A retrovirus carrying a MDR1 cDNA, as described by Pastan et al., *Proc. Natl. Acad. Sci.*, Vol. 85, 4486–4490 (1988). The resistant line, labelled L1210VMDRC.06, was obtained from Dr. M. M. Gottesman of the National Cancer Institute. These drug-resistant transfectants had been selected by culturing cells in 0.06 mg/ml colchicine.

Multi-drug resistance assays were conducted by plating cells ($2\times10^3$, $1\times10^4$, or $5\times10^4$ cells/well) in 96 well microtiter plates and exposing them to a concentration range of doxorubicin (50 nM–10 μM) in the presence or absence of multi-drug resistance modifier compounds ("MDR inhibitors") of this invention (1, 2.5 or 10 μM) as described in Ford et al., *Cancer Res.*, Vol. 50, 1748–1756. (1990). After culture for 3 days, the viability of cells was quantitated using MTT (Mossman) or XTT dyes to assess mitochondrial function. All determinations were made in replicates of 4 or 8. Also see, Mossman T., *J. Immunol. Methods*, Vol. 65, 55–63 (1983).

Results were determined by comparison of the IC$_{50}$ for doxorubicin alone to the IC$_{50}$ for doxorubicin+MDR inhibitor. An MDR ratio was calculated (IC$_{50}$ Dox/IC$_{50}$ Dox+ Inhibitor) and the integer value used for comparison of compound potencies.

In all assays, compounds according to this invention were tested for intrinsic antiproliferative or cytotoxic activity. The results are summarized in Table 1 below. As demonstrated in Table 1, the compounds generally caused <10% cytotoxicity at concentrations of 10 μM or greater. In Table 1, "NT" indicates that the compound was not tested at the respective concentration.

TABLE 1

Evaluation of Compounds for Reversal of MDR

| Compound | IC50 Dox Alone | IC50 Dox + 1 μM Cpd. | IC50 Dox + 2.5 μM Cpd. | MDR Ratio 1.0 μM Cpd. | MDR Ratio (2.5 μM) |
|---|---|---|---|---|---|
| 5 | 700 | 250 | 90 | 2.8 | 7.8 |
| 6 | 950 | NT | 65 | NT | 14.6 |
| 7 | 1000 | 250 | 65 | 4.0 | 15.4 |
| 8 | 2250 | 1200 | 625 | 1.9 | 3.6 |
| 9 | 2250 | 1800 | 325 | 1.3 | 6.9 |
| 10 | 850 | 400 | 85 | 2.1 | 7.8 |
| 11 | 2250 | 1900 | 1000 | 1.2 | 2.3 |
| 13 | 1800 | 600 | 160 | 3.0 | 11.5 |
| 14 | 2250 | 1200 | 625 | 1.9 | 3.6 |
| 16 | 800 | NT | 75 | NT | 10.7 |
| 17 | 950 | NT | 70 | NT | 10.7 |
| 18 | 950 | NT | 70 | NT | 13.6 |
| CsA | 800 | 60 | NT | 13.3 | NT |

EXAMPLE 25

Inhibition of MRP-Mediated MDR

In order to demonstrate that the compounds of this invention are effective in reversing MPR-mediated MDR, in addition to P-glycoprotein-mediated MDR, we assayed inhibition in a non-P-glycoprotein expressing cell line.

We plated HL60/ADR cells in 96 well microtiter plates ($4 \times 10^4$ cells/well). The cells were then exposed to various concentrations of doxorubicin (50 nM to 10 µM) in the presence or absence of various compounds of this invention at various concentrations (0.5–10 µM). After culturing the cells for 3 days, their viability was quantitated using the XTT dye method to assess mitochondrial function. Results were expressed as a ratio of the $IC_{50}$ for doxorubicin alone to the the $IC_{50}$ for doxorubicin plus MDR inhibitor. $IC_{50}$ values are expressed in nM. In all assays the intrinsic antiproliferative or cytotoxicity activity of the MDR inhibitors was also determined for HL60/ADR cells. The results of this assay are set forth in Table 2 below:

TABLE 2

Reversal Of MRP-meidated MDR in HL60/ADR Cells

| Cmpd | $IC_{50}$ Dox alone | $IC_{50}$ Dox + 0.5 µM Cpd | $IC_{50}$ Dox + 1 µM Cpd | $IC_{50}$ Dox + 2.5 µM Cpd | $IC_{50}$ Dox + 5 µM Cpd | $IC_{50}$ Dox + 10 µM Cpd | MDR Ratio 0.5 µM | MDR Ratio 1 µM | MDR Ratio 2.5 µM | MDR Ratio 5 µM | MDR Ratio 10 µM |
|---|---|---|---|---|---|---|---|---|---|---|---|
| 6 | 5.0 | 4 | 3.2 | 0.9 | 0.175 | 0.09 | 1.3 | 1.6 | 5.6 | 28.6 | 55.6 |
| 18 | 5.0 | 4 | 3 | 2.4 | 1.3 | 0.9 | 1.3 | 1.7 | 2.1 | 3.8 | 5.6 |

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

We claim:

1. A compound of formula (I):

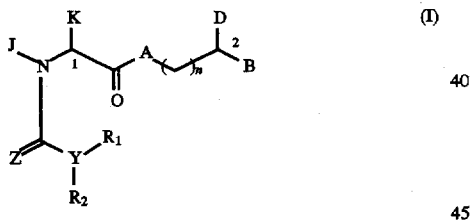

wherein:

A is $CH_2$, oxygen, NH or N—(C1–C4 alkyl);

B and D are independently:

Ar, (C1–C6)-straight or branched alkyl, (C2–C6)-straight or branched alkenyl or alkynyl, (C5–C7)-cycloalkyl substituted (C1–C6)-straight or branched alkyl, (C3–C6)-straight or branched alkenyl or alkynyl, (C5–C7)-cycloalkenyl substituted (C1–C6)-straight or branched alkyl, (C3–C6)-straight or branched alkenyl or alkynyl, Ar-substituted (C1–C6)-straight or branched alkyl, Ar-substituted (C3–C6)-straight or branched alkenyl or alkynyl;

wherein any one of the $CH_2$ groups of said alkyl chains may be optionally replaced by a heteroatom selected from the group consisting of O, S, SO, $SO_2$, and NR;

wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group;

J and K are taken together with the nitrogen and carbon atoms to which they are respectively bound to form a 5–7 membered heterocyclic ring which may contain a heteroatom selected from the group consisting of O, S, SO and $SO_2$;

Z is O or S;

Y is O or N; wherein:

when Y is O, then $R_1$ is a lone pair and $R_2$ is selected from the group consisting of Ar, (C1–C6)-straight or branched alkyl, and (C3–C6)-straight or branched alkenyl or alkynyl; and when Y is N, then $R_1$ and $R_2$ are independently selected from the group consisting of Ar, (C1–C6)-straight or branched alkyl, and (C3–C6)-straight or branched alkenyl or alkynyl; or $R_1$ and $R_2$ are taken together to form a heterocyclic 5–6 membered ring selected from the group consisting of pyrrolidine, imidazolidine, pyrazolidine, piperidine, and piperazine;

wherein Ar is a carbocyclic aromatic group selected from the group consisting of phenyl, 1-naphthyl, 2-naphthyl, indenyl, azulenyl, fluorenyl and anthracenyl;

or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar is optionally substituted with one to three substituents which are independently selected from the group consisting of hydrogen, halogen, hydroxyl, nitro, $SO_3H$, trifluoromethyl, trifluoromethoxy, (C1–C6)-straight or branched alkyl, (C2–C6)-straight or branched alkenyl, O—(C1–C4)-straight or branched alkyl, O—(C3–C4)-straight or branched alkenyl, O-benzyl, O-phenyl, 1,2-methylenedioxy, —$NR_3R_4$, carboxyl, N-, N,N-di-carboxamides, morpholinyl, piperidinyl, O—X, $CH_2$—$(CH_2)_q$—X, O—$(CH_2)_q$—X, $(CH_2)_q$—O—X and CH=CH—X;

wherein $R_3$ and $R_4$ are independently selected from the group consisting of (C1–C6)-straight or branched alkyl, (C3–C6)-straight or branched alkenyl, hydrogen and benzyl; or wherein $R_3$ and $R_4$ can be taken together to form a 5–6 membered heterocyclic ring;

wherein X is selected from the group consisting of 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl and pyrimidyl;

wherein q is 0–2; and n is 0 or 1;

provided that when n is 0; A, Z, and Y are oxygen; J and K together form a six membered piperidine ring; $R_2$ is t-butyl and B is 3-phenylpropyl, then D is not 2-phenylethyl, 2-(3-pyridyl)-ethyl, 3-(2-pyridyl)-propyl, 3-(3-pyridyl)-propyl, or 3-chloropropyl; and provided that when n is 0 or 1; A, Z, and Y are oxygen; J and K together form a six membered piperidine ring; $R_2$ is t-butyl and B is benzyl, then D is not 2-phenylethyl or 3-(3-indolyl)-propyl.

2. A compound selected from the group consisting of:

(S)-1-((3,4,5-Trimethoxyphenyl)-methyl-carbamoyl)-piperidine-2-carboxylic acid 4-pyridin-3-yl-1-(3-pyridin-3-yl-propyl)-butyl ester;

(S)-1-((3-Trifluoromethylphenyl)-methyl-carbamoyl)-piperidine-2-carboxylic acid 4-pyridin-3-yl-1-(3-pyridin-3-yl-propyl)-butyl ester;

(S)-1-((4-Tert-butylphenyl)-methyl-carbamoyl)-piperidine-2-carboxylic acid 4-pyridin-3-yl-1-(3-pyridin-3-yl-propyl)-butyl ester;

(S)-1-((4-Isopropylphenyl)-methyl-carbamoyl)-piperidine-2-carboxylic acid 4-pyridin-3-yl-1-(3-pyridin-3-yl-propyl)-butyl ester;

(S)-1-(Piperidine-1-carbonyl)-piperidine-2-carboxylic acid 4-pyridin-3-yl-1-(3-pyridin-3-yl-propyl)-butyl ester;

(S)-1-((3,4,5-Trimethoxyphenyl)-methyl-carbamoyl)-piperidine-2-carboxylic acid 4-pyridin-1-yl-1-(3-pyridin-1-yl-propyl)-butyl ester;

(S)-Piperidine-1,2-dicarboxylic acid 1-(3,4,5-trimethoxyphenyl) ester 2-(4-pyridin-3-yl-1-(3-pyridin-3-yl-propyl)-butyl) ester;

(S)-Piperidine-2-carboxylic acid 2-(1-(2-phenyl-ethyl)-3-phenyl-propyl ester;

(S)-1-((3,4,5-Trimethoxyphenyl)-methyl-carbamoyl)-piperidine-2-carboxylic acid 1-(2-phenyl-ethyl)-3-phenyl-propyl ester;

4-(Methyl-(2-(1-phenethyl-3-phenyl-propoxycarbonyl)-piperidine-1-carbonyl)-amino)-benzenesulfonic acid;

(S)-Piperidine-2-carboxylic acid 1-benzyloxy-methyl-2-benzyloxyethyl ester;

(S)-1-(Methyl-(4-morpholin-1-yl-phenyl)-carbamoyl)-piperidine-2-carboxylic acid 2-benzyloxy-1-(benzyloxy-methyl)-ethyl ester;

(S)-1-(Methyl-4-piperidin-1-yl-phenyl)-carbamoyl)-piperidine-2-carboxylic acid 2-benzyloxy-1-(benzyloxy-methyl)-ethyl ester;

(S)-Piperidine-1,2-dicarboxylic acid 2-(2-benzyloxy-1-(benzyloxymethyl)-ethyl)ester 1-quinolin-5-yl ester;

(S)-Piperidine-1,2-dicarboxylic acid 2-(2-benzyloxy-1-(benzyloxymethyl)-ethyl)ester 1-pyridin-3-yl ester; and pharmaceutically acceptable derivatives thereof.

3. The compound according to claim 1, wherein, in formula (I), at least one of B or D is independently represented by the formula —(CH$_2$)$_r$—(X)—(CH$_2$)$_s$—Ar, wherein:

r is 1–4;

s is 0–1;

Ar is as defined in claim 1; and each X is independently selected from the group consisting of CH$_2$, O, S, SO, SO$_2$, and NR, wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen atom and the Ar group.

4. The compound according to claim 1, wherein, in formula (I), each Ar is selected from the group consisting of phenyl, 2-pyridyl, 3-pyridyl, 4-pyridyl, indolyl, isoindolyl, quinolinyl, isoquinolinyl, 1,2,3,4-tetrahydroisoquinolinyl, and 1,2,3,4-tetrahydroquinolinyl, wherein said Ar may contain one or more substituents which are independently selected from the group consisting of hydrogen, hydroxyl, nitro, trifluoromethyl, (C1–C6)-straight or branched alkyl, O—, halogen, SO$_3$H, and NR$_3$R$_4$, wherein R$_3$ and R$_4$ are independently selected from the group consisting of (C1–C6)-straight or branched alkyl, (C3–C6)-straight or branched alkenyl, hydrogen and benzyl; or wherein R$_3$ and R$_4$ can be taken together to form a 5–6 membered heterocyclic ring.

5. A compound of formula (II):

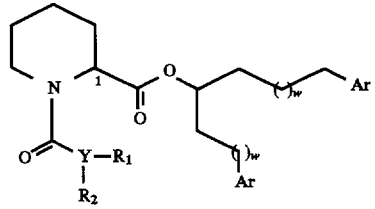

wherein Y, R$_1$, R$_2$ and each Ar are as defined in claim 4, and w is 1 or 2, provided that when Y is oxygen one w and Ar together form a 3-phenylpropyl group, and the other w and Ar together form a 3-(3-pyridyl)propyl, 3-(2-pyridyl)propyl 2-phenylethyl or a 2-(3-pyridyl)ethyl group, then R$_2$ is not t-butyl.

6. A pharmaceutical composition comprising (a) an amount of a compound of formula (I) effective for treatment of multi-drug resistance, wherein said compound is:

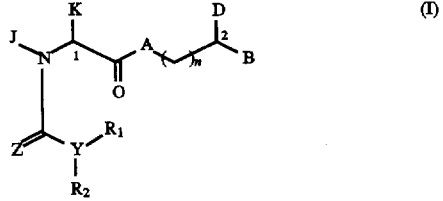

(I)

wherein:

A is CH$_2$ oxygen, NH or N—(C1–C4 alkyl); B and D are independently:

Ar, (C1–C6)-straight or branched alkyl, (C2–C6)-straight or branched alkenyl or alkynyl, (C5–C7)-cycloalkyl substituted (C1–C6)-straight or branched alkyl, (C3–C6)-straight or branched alkenyl or alkynyl, (C5–C7)-cycloalkenyl substituted (C1–C6)-straight or branched alkyl, (C3–C6)-straight or branched alkenyl or alkynyl, Ar-substituted (C1–C6)-straight or branched alkyl, Ar-substituted (C3–C6)-straight or branched alkenyl or alkynyl;

wherein any one of the CH$_2$ groups of said alkyl chains may be optionally replaced by a heteroatom selected from the group consisting of O, S, SO, SO$_2$, and NR;

wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group;

J and K are taken together with the nitrogen and carbon atoms to which they are respectively bound to form a 5–7 membered heterocyclic ring which may contain a heteroatom selected from the group consisting of O, S, SO and $SO_2$;

Z is O or S;

Y is O or N; wherein:

when Y is O, then $R_1$ is a lone pair and $R_2$ is selected from the group consisting of Ar, (C1–C6)-straight or branched alkyl, and (C3–C6)-straight or branched alkenyl or alkynyl; and when Y is N, then $R_1$ and $R_2$ are independently selected from the group consisting of Ar, (C1–C6)-straight or branched alkyl, and (C3–C6)-straight or branched alkenyl or alkynyl; or $R_1$ and $R_2$ are taken together to form a heterocyclic 5–6 membered ring selected from the group consisting of pyrrolidine, imidazolidine, pyrazolidine, piperidine, and piperazine;

wherein Ar is a carbocyclic aromatic group selected from the group consisting of phenyl, 1-naphthyl, 2-naphthyl, indenyl, azulenyl, fluorenyl and anthracenyl;

or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar is optionally substituted with one to three substituents which are independently selected from the group consisting of hydrogen, halogen, hydroxyl, nitro, $SO_3H$, trifluoromethyl, trifluoromethoxy, (C1–C6)-straight or branched alkyl, (C2–C6)-straight or branched alkenyl, O—(C1–C4)-straight or branched alkyl, O—(C3–C4)-straight or branched alkenyl, O-benzyl, O-phenyl, 1,2-methylenedioxy, —$NR_3R_4$, carboxyl, N-, N,N-di-carboxamides, morpholinyl, piperidinyl, O—X, $CH_2$—$(CH_2)_q$—X, O—$(CH_2)_q$—X, $(CH_2)_q$—O—X and CH=CH—X;

wherein $R_3$ and $R_4$ are independently selected from the group consisting of (C1–C6)-straight or branched alkyl, (C3–C6)-straight or branched alkenyl, hydrogen and benzyl; or wherein $R_3$ and $R_4$ can be taken together to form a 5–6 membered heterocyclic ring;

wherein X is selected from the group consisting of 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl and pyrimidyl;

wherein q is 0–2; and n is 0 or 1; and (b) a pharmaceutically acceptable carrier, adjuvant or vehicle.

7. The pharmaceutical composition according to claim 6, further comprising a chemotherapeutic agent.

8. The pharmaceutical composition according to claim 6, further comprising a chemosensitizer.

9. A method for treating multi-drug resistance in a patient comprising the step of administering to said patient a pharmaceutical composition according to any one of claims 6, 7, or 8.

10. A method for treating multi-drug resistance in a patient comprising the step of administering to said patient a pharmaceutical composition comprising a pharmaceutically effective amount of a compound according to claim 3.

11. A method for treating multi-drug resistance in a patient comprising the step of administering to said patient a pharmaceutical composition comprising a pharmaceutically effective amount of a compound according to claim 4.

12. The method according to claim 9, wherein said composition is administered orally.

13. The method according to claim 10 or 11, wherein said composition is administered orally.

14. The method according to claim 9, wherein said multi-drug resistance is P-glycoprotein-mediated.

15. The method according to claim 9, wherein said multi-drug resistance is MRP-mediated.

16. The method according to claim 10 or 11, wherein said multi-drug resistance is P-glycoprotein-mediated.

17. The method according to claim 10 or 11, wherein said multi-drug resistance is MRP-mediated.

18. The pharmaceutical composition according to any one of claims 6, 7 or 8 wherein said compound is selected from:

(S)-1-((3,4,5-Trimethoxyphenyl)-methyl-carbamoyl)-piperidine-2-carboxylic acid 4-pyridin-3-yl-1-(3-pyridin-3-yl-propyl)-butyl ester;

(S)-1-((3-Trifluoromethylphenyl)-methyl-carbamoyl)-piperidine-2-carboxylic acid 4-pyridin-3-yl-1-(3-pyridin-3-yl-propyl)-butyl ester;

(S)-1-((4-Tert-butylphenyl)-methyl-carbamoyl)-piperidine-2-carboxylic acid 4-pyridin-3-yl-1-(3-pyridin-3-yl-propyl)-butyl ester;

(S)-1-((4-Isopropylphenyl)-methyl-carbamoyl)-piperidine-2-carboxylic acid 4-pyridin-3-yl-1-(3-pyridin-3-yl-propyl)-butyl ester;

(S)-1-(Piperidine-1-carbonyl)-piperidine-2-carboxylic acid 4-pyridin-3-yl-1-(3-pyridin-3-yl-propyl)-butyl ester;

(S)-1-((3,4,5-Trimethoxyphenyl)-methyl-carbamoyl)-piperidine-2-carboxylic acid 4-pyridin-1-yl-1-(3-pyridin-1-yl-propyl)-butyl ester;

(S)-Piperidine-1,2-dicarboxylic acid 1-(3,4,5-trimethoxyphenyl) ester 2-(4-pyridin-3-yl-1-(3-pyridin-3-yl-propyl)-butyl) ester;

(S)-Piperidine-2-carboxylic acid 2-(1-(2-phenyl-ethyl)-3-phenyl-propyl ester;

(S)-1-((3,4,5-Trimethoxyphenyl)-methyl-carbamoyl)-piperidine-2-carboxylic acid 1-(2-phenyl-ethyl)-3-phenyl-propyl ester;

4-(Methyl-(2-(1-phenethyl-3-phenyl-propoxycarbonyl)-piperidine-1-carbonyl)-amino)-benzenesulfonic acid;

(S)-Piperidine-2-carboxylic acid 1-benzyloxy-methyl-2-benzyloxyethyl ester;

(S)-1-(Methyl-(4-morpholin-1-yl-phenyl)-carbamoyl)-piperidine-2-carboxylic acid 2-benzyloxy-1-(benzyloxy-methyl)-ethyl ester;

(S)-1-(Methyl-(4-piperidin-1-yl-phenyl)-carbamoyl)-piperidine-2-carboxylic acid 2-benzyloxy-1-(benzyloxy-methyl)-ethyl ester;

(S)-Piperidine-1,2-dicarboxylic acid 2-(2-benzyloxy-1-(benzyloxymethyl)-ethyl)ester 1-quinolin-5-yl ester; or (S)-Piperidine-1,2-dicarboxylic acid 2-(2-benzyloxy-1-(benzyloxymethyl)-ethyl)ester 1-pyridin-3-yl ester.

19. A method for treating multi-drug resistance in a patient comprising the step of administering to said patient a pharmaceutical composition according to claim 18.

* * * * *

UNITED STATES PATENT AND TRADEMARK OFFICE
CERTIFICATE OF CORRECTION

PATENT NO : 5,744,485
DATED : April 28, 1998
INVENTION(S) : Robert E. Zelle, et al.

It is certified that error appears in the above-identified patent and that said Letters Patent are hereby corrected as shown below:

Column 1, line 45, delete "brast" and substitute therefor
-- breast --.
Column 3, line 6 delete "$S_2$" and substitute therefor -- $SO_2$ --.
Column 6, Scheme 1, delete "  " and substitute therefor -- 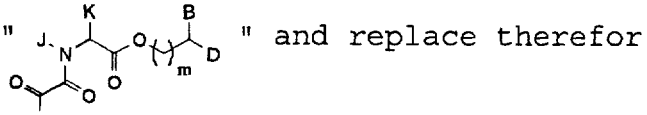 --.

Column 6, Scheme 1, delete "  " and replace therefor
-- 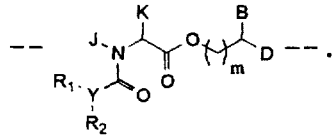 --.

Column 8, line 10 delete "intreating of" and substitute therefor
-- in treating or --.
Column 8, line 13 delete "humans.And" and substitute therefor
-- humans, and --.
Column 12, line 44 delete "(m. 2H)" and substitute therefor
-- (m, 2H) --.
Column 12, line 47 delete "153" and substitute therefor --1.53--.
Column 13, line 3 delete "(m. 2H)" and substitute therefor
-- (m, 2H) --.
Column 13, line 4 delete "2.64-2.52 m," and substitute therefor
-- 2.64-2.52 (m, --.
Column 13, line 17 delete "(d. 2H)" and substitute therefor
-- (d, 2H) --.
Column 17, line 9 delete the second occurrence of "the".
Column 17, Table 2 delete "MRP-meidated" and substitute therefor
-- MRP-mediated --.
Column 20, line 18 delete "O-," and substitute therefor

UNITED STATES PATENT AND TRADEMARK OFFICE
CERTIFICATE OF CORRECTION

PATENT NO. : 5,744,485
DATED : April 28, 1998
INVENTOR(S) : Robert E. Zelle, et al.

It is certified that error appears in the above-indentified patent and that said Letters Patent is hereby corrected as shown below:

```
Column 20, line 18 delete "O-," and substitute therefor
-- O-[(C1-C6)-straight or branched alkyl], --.
```

Signed and Sealed this

Twenty-seventh Day of March, 2001

Attest:

NICHOLAS P. GODICI

*Attesting Officer*      *Acting Director of the United States Patent and Trademark Office*